(12) United States Patent
Banik (10) Patent No.: US 10,933,202 B1
(45) Date of Patent: Mar. 2, 2021

(54) INDICATOR MEMBER OF LOW STRENGTH RESISTANCE FOR A TAMPER EVIDENT CLOSURE

(71) Applicant: Robert Banik, Ft. Lauderdale, FL (US)

(72) Inventor: Robert Banik, Ft. Lauderdale, FL (US)

(73) Assignee: INTERNATIONAL MEDICAL INDUSTRIES INC., Pompano Beach, FL (US)

( * ) Notice: Subject to any disclaimer, the term of this patent is extended or adjusted under 35 U.S.C. 154(b) by 57 days.

(21) Appl. No.: 15/985,498

(22) Filed: May 21, 2018

Related U.S. Application Data (60) Provisional application No. 62/508,638, filed on May 19, 2017.

(51) Int. Cl.
  *A61M 5/50* (2006.01)
  *A61J 1/20* (2006.01)
  *A61M 5/31* (2006.01)

(52) U.S. Cl.
  CPC .......... *A61M 5/5086* (2013.01); *A61J 1/2096* (2013.01); *A61M 2005/312* (2013.01)

(58) Field of Classification Search
  CPC ...... A61M 5/5086; A61M 5/508; A61M 5/50; A61M 2005/312; A61M 2005/3117; A61M 5/321; A61M 2005/3104; A61M 2005/3106; A61J 1/2096; A61J 1/14; A61J 1/20
  See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |

(Continued)

FOREIGN PATENT DOCUMENTS

| | | |
|---|---|---|
| EP | 0148116 A | 7/1985 |
| WO | WO 2008/000279 | 1/2008 |
| WO | WO 2017086607 | 5/2015 |

*Primary Examiner* — Nathan R Price
*Assistant Examiner* — Courtney B Fredrickson
(74) *Attorney, Agent, or Firm* — Malloy and Malloy, P.L.; Jennie Malloy (57) ABSTRACT

A tamper evident closure, intended primarily for a luer-slip or like frictional connection between one or more components associated with the closure and a syringe or other medical device, includes a housing having an open end and a tip cap disposed within the housing. An indicator member is connected to the housing in at least partially covering relation to the open end and includes an access opening disposed in accessible relation with the tip cap. A cover is removably disposed in overlying engagement with at least a portion of said indicator member in covering relation to the access opening. The indicator member has an inner segment disposed in contiguous surrounding relation to the access opening and has a reduced breakaway resistance, capable of being easily ruptured, ripped or torn during passage of said tip cap through the access opening, concurrent to the tip cap being connected to the medical device.

22 Claims, 5 Drawing Sheets

(56) References Cited

U.S. PATENT DOCUMENTS

| | | | |
|---|---|---|---|
| 2,888,015 A | 5/1959 | Hunt | |
| 2,952,255 A | 9/1960 | Hein, Jr. | |
| 3,122,280 A | 2/1964 | Goda | |
| 3,245,567 A | 4/1966 | Knight | |
| 3,323,798 A | 6/1967 | Miller | |
| 3,364,890 A | 1/1968 | Andersen | |
| 3,368,673 A | 2/1968 | Johnson | |
| 3,598,120 A | 8/1971 | Mass | |
| 3,610,241 A | 10/1971 | LeMarie | |
| 3,700,215 A | 10/1972 | Hardman et al. | |
| 3,706,307 A | 12/1972 | Hasson | |
| 3,712,749 A | 1/1973 | Roberts | |
| 3,747,751 A | 7/1973 | Miller et al. | |
| 3,872,867 A | 3/1975 | Killinger | |
| 3,904,033 A | 9/1975 | Haerr | |
| 3,905,375 A | 9/1975 | Toyama | |
| 3,937,211 A | 2/1976 | Merten | |
| 4,005,739 A | 2/1977 | Winchell | |
| 4,043,334 A | 8/1977 | Brown et al. | |
| 4,046,145 A | 9/1977 | Choksi et al. | |
| 4,068,696 A | 1/1978 | Winchell | |
| 4,216,585 A | 8/1980 | Hatter | |
| 4,216,872 A | 8/1980 | Bean | |
| 4,244,366 A | 1/1981 | Raines | |
| 4,252,122 A | 2/1981 | Halvorsen | |
| 4,271,972 A | 6/1981 | Thor | |
| 4,286,591 A | 9/1981 | Raines | |
| 4,286,640 A | 9/1981 | Knox et al. | |
| 4,313,539 A | 2/1982 | Raines | |
| 4,369,781 A | 1/1983 | Gilson et al. | |
| 4,420,085 A | 12/1983 | Wilson et al. | |
| 4,430,077 A | 2/1984 | Mittleman et al. | |
| 4,457,445 A | 7/1984 | Hanks et al. | |
| D277,783 S | 2/1985 | Beck | |
| 4,521,237 A | 6/1985 | Logothetis | |
| 4,530,697 A | 7/1985 | Kuhlemann et al. | |
| 4,571,242 A | 2/1986 | Klein et al. | |
| 4,589,171 A | 5/1986 | McGill | |
| 4,664,259 A | 5/1987 | Landis | |
| 4,667,837 A | 5/1987 | Vitello et al. | |
| 4,676,530 A | 6/1987 | Nordgren et al. | |
| 4,693,707 A | 9/1987 | Dye | |
| 4,726,483 A | 2/1988 | Drozd | |
| 4,743,229 A | 5/1988 | Chu | |
| 4,743,231 A | 5/1988 | Kay et al. | |
| 4,760,847 A | 8/1988 | Vaillancourt | |
| 4,813,564 A | 3/1989 | Cooper et al. | |
| 4,832,695 A | 5/1989 | Rosenberg et al. | |
| 4,834,706 A | 5/1989 | Beck et al. | |
| 4,842,592 A | 6/1989 | Caggiani et al. | |
| 4,844,906 A | 7/1989 | Hermelin et al. | |
| 4,906,231 A | 3/1990 | Young | |
| 4,919,285 A | 4/1990 | Roof et al. | |
| 4,936,445 A | 6/1990 | Grabenkort | |
| 5,009,323 A | 4/1991 | Montgomery et al. | |
| 5,049,129 A | 9/1991 | Zdeb et al. | |
| 5,057,093 A | 10/1991 | Clegg et al. | |
| D323,392 S | 1/1992 | Byrne | |
| 5,135,496 A | 8/1992 | Vetter et al. | |
| 5,165,560 A | 11/1992 | Ennis, III et al. | |
| 5,230,429 A | 7/1993 | Etheredge, III | |
| 5,267,983 A | 12/1993 | Oilschlager et al. | |
| 5,292,308 A | 3/1994 | Ryan | |
| 5,293,993 A | 3/1994 | Yates, Jr. et al. | |
| 5,295,599 A | 3/1994 | Smith | |
| 5,312,367 A | 5/1994 | Nathan | |
| 5,312,368 A | 5/1994 | Haynes | |
| 5,328,466 A | 7/1994 | Denmark | |
| 5,328,474 A | 7/1994 | Raines | |
| 5,356,380 A | 10/1994 | Hoekwater et al. | |
| 5,380,295 A | 1/1995 | Vacca | |
| 5,405,339 A | 4/1995 | Kohnen et al. | |
| 5,456,668 A | 10/1995 | Ogle, II | |
| 5,458,580 A | 10/1995 | Hajishoreh | |
| 5,468,224 A | 11/1995 | Souryal | |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |

(56) References Cited

U.S. PATENT DOCUMENTS

| | | | |
|---|---|---|---|
| 7,482,166 B2 | 1/2009 | Nollert et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 * | 8/2012 | Ferlic ............... A61M 39/20 |
| | | 422/309 |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,376,655 B2 | 8/2019 | Pupke et al. |
| D859,125 S | 9/2019 | Weagle et al. |
| 10,758,684 B1 | 9/2020 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 * | 4/2008 | Buehler ............... A61M 5/50 |
| | | 604/111 |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |

(56) References Cited

U.S. PATENT DOCUMENTS

| | | |
|---|---|---|
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1* | 7/2015 | Okihara ............... A61B 50/22 206/366 |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1* | 1/2017 | Duinat ............... A61M 5/3137 |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

* cited by examiner

INDICATOR MEMBER OF LOW STRENGTH RESISTANCE FOR A TAMPER EVIDENT CLOSURE

CLAIM OF PRIORITY

The present application is based on and a claim of priority is made under 35 U.S.C. Section 119(e) to a provisional patent application that is currently in the U.S. Patent and Trademark Office, namely, that having Ser. No. 62/508,638 and a filing date of May 19, 2017, which is incorporated herein by reference in its entirety.

BACKGROUND OF THE INVENTION

Field of the Invention

This invention is directed to a tamper evident closure for a medical device which includes an indicator member disposed in overlying relation to an open end of the housing. At least a portion of the indicator member comprises a material having a predetermined low-strength breakaway resistance, which is easily ruptured upon removal of a tip cap from the interior of the housing, concurrent to its being frictionally connected to a medical device.

Description of the Related Art

In the medical field, it is a relatively common for authorized medical personnel to prescribe a drug or medication for a patient which will be given to the patient by an injection or other procedure, including administering fluids to the patient by intravenous (IV) infusion. It is also relatively common for syringes and other drug administering devices to be pre-loaded or filled by a pharmacist or other authorized personnel, whether within the hospital or at another facility and location, at what may be generally referred to as a filling station. However, a filling station is typically located in a remote part of the hospital or other facility, relative to the patient care area where the injection is to be administered. Indeed, at large medical facilities, a filling station may resemble a factory on the hospital grounds from which drugs and other fluids are delivered to multiple nursing stations within the hospital at different locations. Because of the remote location of many nurse's stations relative to a filling station, a fluid or drug loaded administering device is very often given to another person for delivery to a nurse's station for subsequent dosing of the patient by a duly qualified nurse or other medically trained person. As a result, a pre-loaded syringe may travel quite some distance and be handled by several people before it reaches a nurse's station, which raises some concern that the contents of the syringe may be tampered with or cause the sterility of the syringe and/or its contents to be compromised.

Additionally, in the case where a drug has been prescribed that is a very expensive or addictive, such as but not limited to morphine, which has been pre-loaded in the syringe or other administering device, there is a danger that the pre-loaded syringe or other administering device will be tampered with at some point, by a person seeking unauthorized access to the drug. This possibility can present a real danger if such a person were to gain access to the prescribed medicine and then, inappropriately and without concern, substitute some other, unauthorized material in the syringe which looks like the actual prescribed medicine and dosage. By way of an example only, if saline solution or water or another drug were substituted for a dose of morphine, the patient would not receive the prescribed drug which by itself, could be quite harmful, while the substituted content might potentially also cause serious harm. Thus, there is a problem of knowing if a sealed, pre-loaded syringe or other administering device has, or has not, been exposed to contamination or might otherwise have been compromised by its being tampered with. This and related types of problems have been described in one or more previously issued U.S. patents owned by the Applicant/Assignee herein, such as U.S. Pat. No. 5,328,474.

More specifically, and in order to overcome the disadvantages and concerns associated with the growing use of syringes and/or other medical devices that are pre-filled with various prescribed medicines, the Applicant/Assignee herein has developed a variety of "tamper evident closures". Such tamper evident closures are structured to prevent or at least restrict access to the prescribed medicine or other contents within a pre-filled syringe. If in fact, access has been accomplished or even attempted to a pre-filled syringe or other drug administering device, such tamper evident closures are intended to provide a clear indication of having been tampered with.

However, as the technology associated with tamper evident closures evolves, particularly with drug compounding and admixing, a need has also evolved for tamper evident closures of the type referred to herein to prevent drug misuse associated with medical devices having a luer type of connection, such as a "luer slip" fitting. That is, while some tamper evident closures are also known to incorporate a luer connection between portions of the tamper evident closure and the medical device to which it is attached, there remains a need for improvements as the classic luer slip fitting does not have luer lock threads or features to allow such known tamper evident closure to remain on the medical device without relying on alternate means. For example, many such luer connectors such as, but not limited to a luer-slip connection, are based primarily on frictional engagement between male and female luer connector members. As a result, there is a need in this area for a tamper evident closure which incorporates a multi-layer component, capable of evidencing tampering or use of the closure in a manner which does not detach the medical device from a tamper evident closure, which might happen when the connection therebetween is a frictional type of connection. If a new tamper evident closure were developed for this purpose, it should also offer some savings of both time and cost in the overall manufacture/assembly of any such tamper evident closure as well as in the installation on a pre-filled syringe or other medical device.

SUMMARY OF THE INVENTION

The present invention is directed to a tamper evident closure structured to be connected to a medical device such as, but not limited to, a pre-filled syringe. As such, the tamper evident closure includes a housing having a substantially hollow interior and at least one open end disposed in communication with the hollow interior. The tamper evident closure also includes a tip cap or like member structured to be directly connected to a corresponding connecting portion of the medical device, and in most cases will be in closing, sealing relation thereto. As explained in greater detail hereinafter, the tip cap and the corresponding connecting portion of the medical device may be cooperatively structured to define a "luer-slip" connection therebetween.

The present invention includes an indicator member secured to the housing, at said open end and in at least partially covering relation thereto. The indicator member, which may have a plurality of layers, includes an access opening defined by at least one aperture formed therein and extending there-through so as to be into communicating relation with the interior of the housing. The access opening is also disposed in direct accessible relation to the tip cap when disposed within the housing. Accordingly, a connection or attachment of the tip cap to the nozzle or connecting portion of the syringe or medical device is accomplished by extending the connecting portion of the syringe or medical device through the access opening and into engaging relation with the tip cap.

As also explained in greater detail hereinafter, the indicator member having at least one aperture that defines the access opening is specifically dimensioned to facilitate passage of the nozzle or connecting portion of the syringe or medical device there-through into engaging, connecting relation to the tip cap. However, in contrast, the diameter or transverse dimension of the access opening is smaller than that of at least a portion of the tip cap. As a result, the tip cap, when connected to the syringe or medical device, will not be able to freely pass back through the access opening to an exterior of the housing, due to the comparative smaller transverse dimension of the access opening relative to the tip cap.

At least one feature of the tamper evident closure of the present invention comprises the indicator member being at least partially formed of a material that is comparatively weak and has a low strength resistance, and more specifically, comprises a predetermined, low-strength breakaway resistance. Such material may include, but not be limited to, a paper-based material, a tape-based material or other comparatively low strength materials, and in one embodiment, may comprise a die-cut, multi-layer tape that can be peeled or ripped relatively easily. In another embodiment of a paper based material, the paper design can be relatively thin and influenced with simple die-cut geometry and paper thickness. Further, the term "predetermined low-strength breakaway resistance" may be at least partially defined as a material of sufficiently low strength or resistance to enable a tip cap associated with the tamper evident closure assembly to pass through the access opening, while connected to the syringe or medical device by virtue of a luer-slip connection or frictional-type connection.

Accordingly, the tamper evident features of the closure assembly of the present invention are at least partially defined by a rupturing, tearing, ripping, etc. of at least a portion of the indicator member disposed in surrounding relation to the access opening. As indicated, the larger comparative dimension of the tip cap, relative to that of the access opening, will prevent a free passage of the tip cap through the access opening upon being connected to the medical device. Therefore, in order to remove the tip cap from the interior of the housing, at least a portion of the indicator member will be ruptured, torn, ripped, etc. As a result, the indicator member will no longer be in an "intact orientation" due to its being ruptured, torn, ripped etc. by the forced passage of the tip cap through the access opening, concurrent to its being connected to the medical device.

As is already known, a luer-slip connection is established and maintained due to a frictional engagement between male and female connecting portions. Further, the luer-slip connection, as classically recognized and as used herein is meant to describe a luer fitting/connection that does not have luer lock threads or like locking structures or features. As a result, attachment between the luer connectors in a luer-slip connection structure relies primarily on frictional engagement to establish and maintain the connection.

In relation to the structural features of the present invention, the "predetermined, low-strength breakaway resistance" of at least a portion of the indicator will allow passage of the tip cap through the access opening when attached to the medical device by such a luer-slip or other frictional connection, without causing a detachment of the luer slip or other frictional connection between the tip cap and the medical device. In contrast, a conventional barrier or indicator member formed of a strong material, when positioned in a removal restricting engagement with an interior tip cap, would cause a disconnection of the tip cap from the medical device because of the aforementioned frictional connection therebetween and the comparatively high-strength of the conventionally structured indicator or like removable restricting barrier. For purposes of clarity, a conventional or known indicator member associated with a housing of a tamper evident closure may be formed as an injection molded design from a high strength plastic-type material, the increased strength and resistance which would cause a disconnection of the tip cap from the medical device when the connection therebetween is a frictional-based connection.

Additional structural and operative features of one or more preferred embodiments of the tamper evident closure of the present invention includes the indicator having an outer segment fixedly secured to the open end, such as about a peripheral ridge and/or outer peripheral portion of the housing surrounding the open end. As such, the indicator member also includes an integrally or otherwise fixedly attached inner segment, which is disposed in surrounding, contiguous relation to the aforementioned at least one aperture defining the access opening. In order to facilitate the above noted tamper evident features, at least the inner segment is formed of the material structured to demonstrate the predetermined, low-strength breakaway resistance, as set forth above and in further detail herein.

Yet additional features of the one or more preferred embodiments of the tamper evident closure includes a cover interconnected to the housing by being attached to the housing or to a portion of the indicator member such as, but not limited to, the outer segment thereof. Therefore, the cover is disposed in overlying, covering relation to at least a portion of the indicator member and in covering relation to the access opening. Attachment of the cover in this preferred position may be accomplished by a removable adhesive which facilitates the cover being peeled away from its overlying, covering position to the access opening and indicator member.

In order to facilitate the establishment and maintenance of a sterile environment of at least the tip and/or the interior of the housing, the cover may be at least partially formed from a gas permeable material, such as but not limited to Tyvek®, which allows a sterilizing gas medium to pass there through. Such a sterilizing gas may be in the form of ethylene trioxide (ETO) or other appropriate sterilizing medium.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented throughout the accompanying Figures, the present invention is directed to a tamper evident closure generally indicated as 10. The tamper evident closure 10 includes an external housing 12 having a substantially hollow interior 14, as partially shown in FIG. 1B, and more clearly represented in FIG. 2. The housing or sleeve 12 includes a closed end or bottom, which may be formed by a single injection mold which will help in terms of saving both expense and assembly time.

Figure 2:
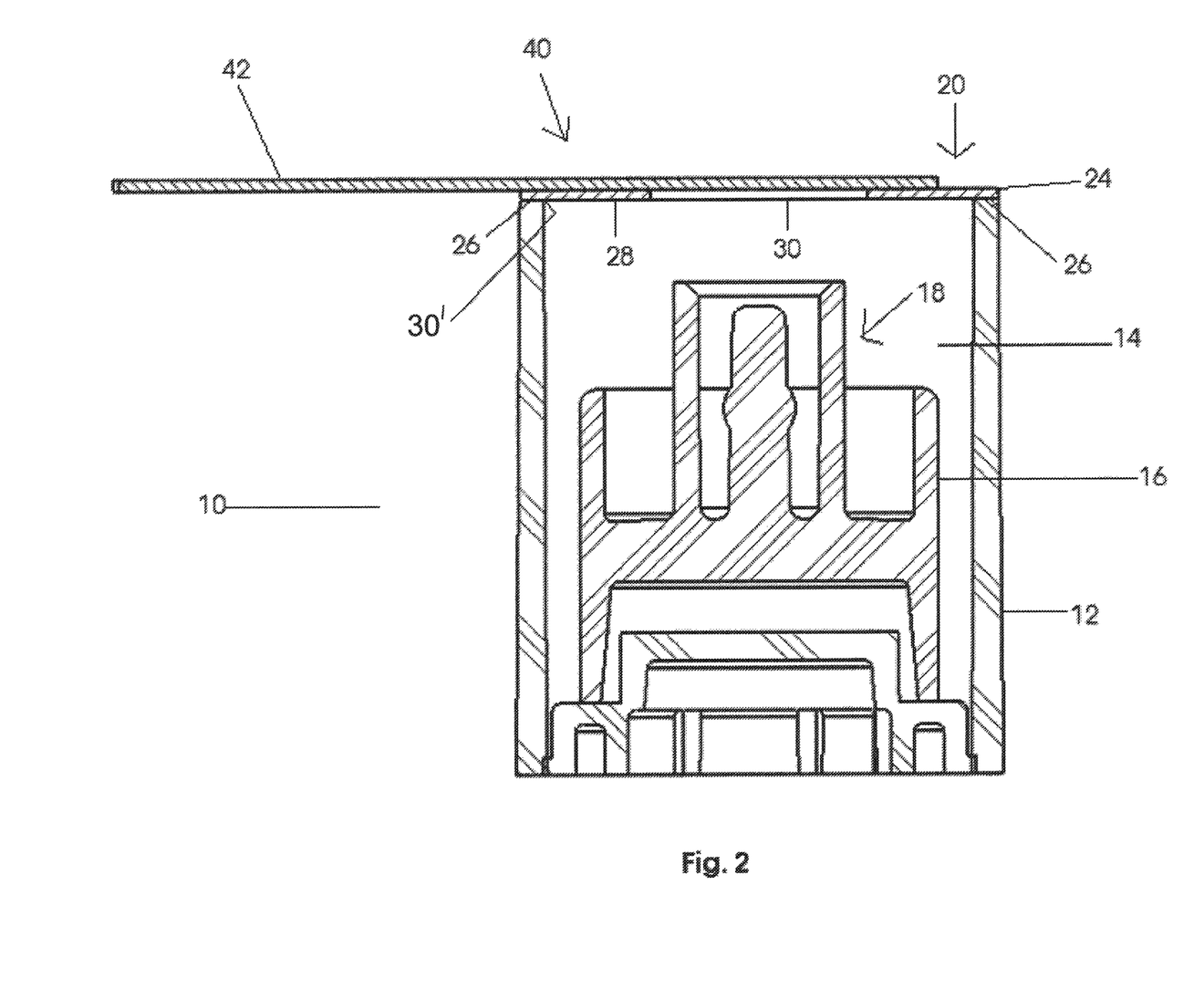
FIG. 2 is an interior sectional view of the embodiment of FIG. 1.
Figure 4:
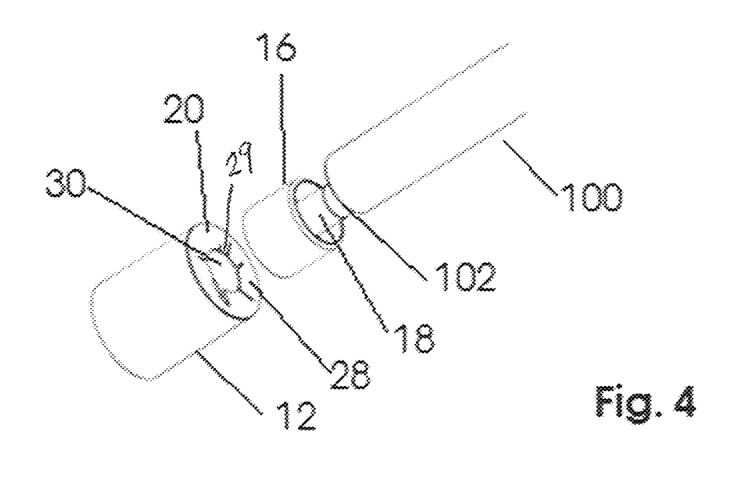
FIG. 4 is a perspective view in partial cutaway of the removal of a tip cap of the tamper evident closure from an interior of the housing associated with the closure, concurrent to being attached to the medical device.

In addition, the tamper evident closure 10 includes a closure, preferably in the form of a tip cap 16, shown in FIGS. 2 and 4, that is removably disposed within the interior 14 of the housing 12. As indicated in FIG. 2 and described subsequently herein, the tip cap 16 may also be movably disposed within the housing 12.

With reference to FIG. 2, the tip cap 16 may be structured to include a luer connector, preferably in the form of a luer-slip connector generally indicated as 18, as also illustrated in FIG. 4. In cooperation therewith, a medical device, such as a syringe generally indicated as 100 in FIGS. 3A-3C and 4, which has been pre-filled with a medicine or prescription drug includes a connecting portion or nozzle 102, that may be in the form of a Luer connector. As such the connecting portion 102 of the syringe or medical device 100 and the luer connector 18 associated with the tip cap 16, shown inside the housing 14 in FIG. 2, may be cooperatively structured to define a luer-slip connection or other frictional-type of connection therebetween. However, and for reasons to be explained in greater detail hereinafter, the attachment between the tip cap 16 and the medical device 100 may be other than a luer-slip connection. Such additional type connections may include those commonly associated with a tip cap which is structured to be connected to a medical device intended for use as an oral administration device and/or for medical devices associated with Enteral and/or Neuraxial administration.

Figure 1A:
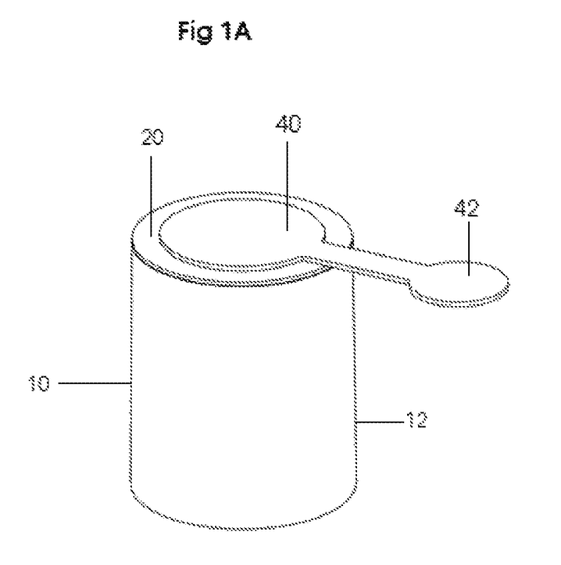
FIG. 1A is a front perspective view of a tamper evident closure according to the present invention in a first preferred embodiment.
Figure 1B:
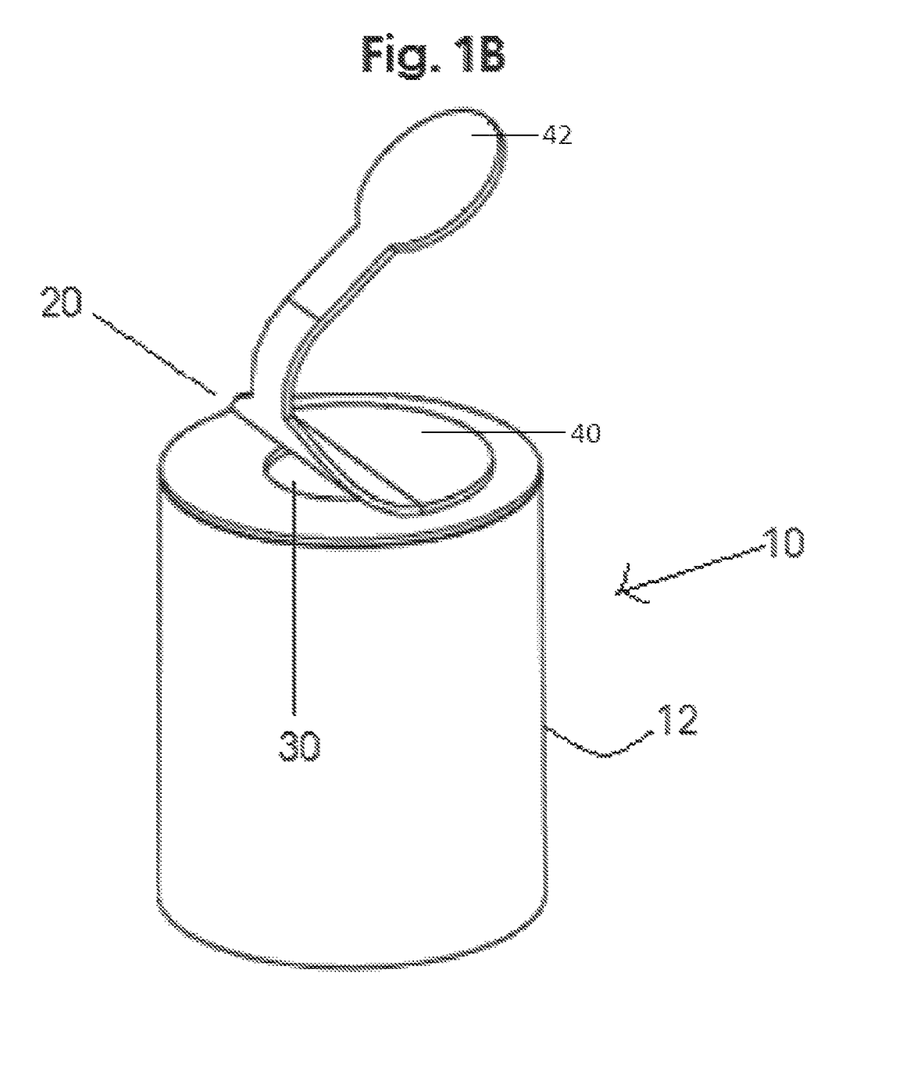
FIG. 1B is a front perspective view of the embodiment of FIG. 1A but illustrating an at least partially opened state.
Figure 3A:
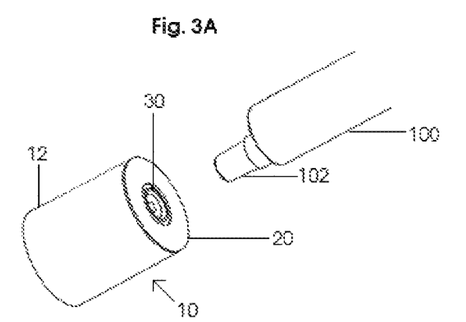
FIG. 3A is a perspective view in partial exploded form of the tamper evident closure similar to the embodiment of FIGS. 1A, 1B and 2, but illustrating the closure in position for being connected to a medical device.
Figure 3B:
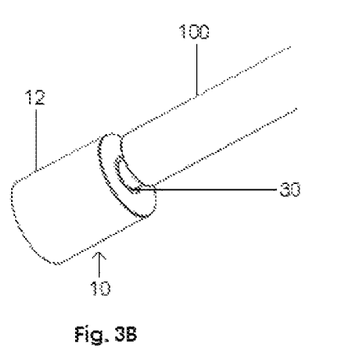
FIG. 3B is also a perspective view in partial cutaway of the invention as shown in FIG. 3A, but illustrating the tamper evident closure as being connected to the medical device.
Figure 3C:
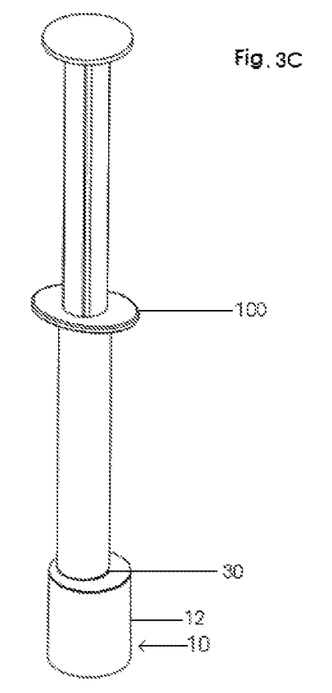
FIG. 3C is a perspective view of the tamper evident closure of the present invention connected to the medical device.

As perhaps best illustrated in FIGS. 1B and 3A, additional structural features of the tamper evident closure 10 according to the present invention include the housing 12 having at least one open end 30' which is disposed in communicating relation with the interior 14 thereof. Also, as represented in FIG. 2, the tamper evident closure 10 includes an indicator member 20 including an outer segment 24 fixedly attached to the outer peripheral portion or ridge 26 of the housing 12, which is disposed in surrounding relation to the open end 30'. The indicator member 20 also includes an inner segment 28 integrally or otherwise secured to the outer segment 24 and extending radially inward therefrom in at least partially overlying, covering relation to the open end 30'.

The indicator member 20 also includes an access opening 30 formed in the inner segment 28 and disposed in communicating relation with the interior 14 of the housing 12 and in accessible relation to the tip cap 16 and connector 18 associated therewith. As also represented throughout the Figures, the access opening 30 is dimensioned to allow passage there-through of the connecting portion 102 of the medical device 100 into connecting engagement with the tip cap 16, and more specifically, the connector 18 associated therewith. As such, the access opening 30 has an at least minimally greater diameter or transverse dimension than that of the connecting portion 102 associated with the syringe or medical device. However, the access opening 30 has a smaller diameter or transverse dimension than at least a portion of the tip cap 16. As a result, the tip cap 16 will not be able to freely pass through the access opening 30 while the indicator member 20, or at least the inner segment 28 thereof, remains in an "intact orientation".

As represented in FIG. 4, the tamper evident features of the closure assembly 10 of the present invention are at least partially defined by a rupturing, tearing, ripping, etc. of at least a portion of the indicator member 20, such as the inner segment 28, which as described above, is disposed in surrounding relation to the access opening 30. As indicated, the larger comparative dimension of the tip cap 16, relative to that of the access opening 30 will prevent the free passage of the tip cap 16 through the access opening 30, such as when connected to the syringe or medical device 100. Therefore, in order to remove the tip cap 16 from the interior 14 of the housing 12, at least the inner segment 28 of the indicator member 20 will be ruptured, torn, ripped, etc. As a result, the indicator member will no longer be in an "intact orientation" due to its having been ruptured, torn, ripped etc. by the forced passage of the tip cap 16 through the access opening 30 concurrent to it being connected to the connecting portion 102 of the syringe or medical device 100. As shown in FIG. 4, the indicator member 20 is noticeably ripped as at 29 and can serve as a signal that tampering has occurred.

Therefore, at least one feature of the tamper evident closure 10 of the present invention comprises the indicator member 20 being at least partially formed of a material structured to include a predetermined, low-strength breakaway resistance. Such material may include, but not be limited to, a paper-based material, a tape-based material, a thin or lightweight plastic capable of being torn or ripped and/or other comparatively low strength materials. Further, the term "predetermined low-strength breakaway resistance" may be defined as a material of sufficiently low strength or resistance, which would enable a tip cap 16 to pass through the access opening 30, while connected to the medical device 100 by virtue of a luer-slip connection or other comparatively "weak" frictional connections, between the luer connecting segments 18 of the tip cap 16 and the connecting portion 102 of the syringe or medical device 100.

In more specific terms, it is already known that a luer-slip connector/connection is typically established and maintained due to a frictional engagement between male and female connecting portions, such as at 18 and 102, respectively. Further, the classic luer-slip connection, as recognized and as used herein is a luer slip fitting/connection that does not have luer lock threads or other locking structures or features. As a result, attachment between the Luer connectors 18 and 102 in a luer-slip connection structure relies primarily on frictional engagement to establish and maintain the connection.

In relation to the structural features of the present invention, the "predetermined, low-strength breakaway resistance" of at least a portion of the indicator member 20 will allow passage of the tip cap 16 through the access opening 30 when attached to the syringe or medical device 100 by such a luer-slip or other frictional connection. In contrast, a conventional barrier or other type indicator member, that does not have such low-strength resistance features, when positioned in a removal restricting engagement with an interior tip cap, would cause a disconnection of the tip cap from the syringe or medical device 100 because of the aforementioned, more easily separated frictional connection therebetween.

For purposes of clarity, a conventional or known indicator member associated with the open end of a housing of a tamper evident closure may be formed as an injection molded design, and thereby includes a relatively high strength, plastic-type material, which is quite different from an indicator member formed of a paper-based material or tape-based material to form a barrier with an ability to be ripped or torn. Such conventional indicator members would require a stronger or increased resistance in order to cause a disconnection from the medical device, when the connection therebetween is a frictional-based connection such as, but not limited to a luer-slip connection.

In contrast, however, a feature of the present invention is to form the indicator member 20 from a pre-determined, low-strength breakaway material and further, to allow use with a tip cap 16 and medical device 100 formed of another material and having higher strength for their interconnection. More specifically, if a luer-slip or other frictional type connection can cause a rupturing, tearing, etc. of the low strength breakaway material of the indicator member 20, the higher strength connectors between the tip cap and the medical device would also serve to rupture, tear, etc. the predetermined, low-strength breakaway resistance material of the indicator member 20.

Yet additional features of the inventive tamper evident closure 10 includes a cover, generally indicated as 40 and shown in FIGS. 1A, 1B and 2, interconnected to the housing 12 by being attached to the housing 12 or to a portion of the indicator member 20 such as, but not limited to the outer surface of the indicator member 20, including but not limited to the outer segment 24. Therefore, the cover 40 is disposed in overlying, covering relation to at least a portion of the indicator member 20 and in covering relation to the access opening 30. Attachment of the cover 40 in this preferred position may be accomplished by a removable adhesive which facilitates an undersurface of the cover 40 being disposed in removable adhered engagement with at least an outer surface portion of the indicator member 20 such as, but not limited to an outer surface portion of the outer segment 24. Such a removable adhesive interconnection thereby facilitates the cover 40 being peeled away from its overlying engagement with at least a portion of the indicator member 20 and its covering relation to the access opening 30, such as is shown in FIG. 1B. The peeling and/or release of the cover 40 from its overlying engagement with the indicator member 20 and covering relation to the access opening 30 may be accomplished by exerting an appropriate force on an outwardly extending pull tab 42 connected to a remainder of the cover 40, as is also clearly represented in FIGS. 1A, 1B and 2.

Additionally, and in order to facilitate the establishment and maintenance of a sterile environment of at least the tip cap 16 and/or the interior 14 of the housing 12, the cover 40 may be at least partially formed from a gas permeable material, such as Tyvek®, which allows a sterilizing gas medium to pass there-through. Such a sterilizing gas may be in the form of ethylene trioxide (ETO) or other appropriate sterilizing medium.

Since many modifications, variations and changes in detail can be made to the described preferred embodiment of the invention, it is intended that all matters in the foregoing description and shown in the accompanying drawings be interpreted as illustrative and not in a limiting sense. As one non-limiting example, the inventive tamper evident closure could utilize perforations within and as part of the indicator member 20, with a portion thereof remaining visible on the syringe 100 or medical device and tip cap 16 once removed from the housing 12. Thus, the scope of the invention should be determined by the appended claims and their legal equivalents.

What is claimed is:

1. A tamper evident closure for a medical device comprising:
    a housing including a hollow interior and an open end disposed in communication with said hollow interior,
    an indicator member, including an access opening, secured to an outer peripheral ridge of said open end of said housing in overlying, at least partially covering relation to said open end,
    a tip cap disposed within said housing in accessible relation to the medical device through said access opening,
    a cover removably connected to an outer surface of said indicator member in overlying, covering relation to said access opening, and
    said indicator member formed of a rupturable material structured to rupture upon passage of said tip cap through said access opening.

2. The tamper evident closure as recited in claim 1 wherein said tip cap includes a luer-slip connector segment.

3. The tamper evident closure as recited in claim 2 wherein said luer-slip connector segment is cooperatively structured with the medical device to define a luer slip connection therebetween.

4. The tamper evident closure as recited in claim 3 wherein said rupturable material is structured to rupture said indicator member upon passage of said tip cap through said access opening, concurrent to the luer slip connection with said medical device.

5. The tamper evident closure as recited in claim 1 wherein said indicator member includes an outer segment fixedly connected to said outer peripheral ridge of said open end of said housing.

6. The tamper evident closure as recited in claim 5 wherein said indicator member further comprises an inner segment directly connected in contiguous relation to and extending inward from said outer segment in overlying and at least partially covering relation to said open end of said housing.

7. The tamper evident closure as recited in claim 6 wherein said access opening comprises at least one aperture formed in said inner segment in communicating relation with said hollow interior.

8. The tamper evident closure as recited in claim 7 wherein said at least one aperture is disposed and dimensioned to facilitate passage therethrough of the medical device, into accessible relation with said tip cap.

9. The tamper evident closure as recited in claim 8 wherein said at least one aperture includes a smaller transverse dimension than that of said tip cap, said at least one aperture dimensioned to restrict passage therethrough of said tip cap concurrent to an intact configuration of said inner segment.

10. The tamper evident closure as recited in claim 1 wherein said indicator member includes an inner segment and an aperture formed through said inner segment, said aperture at least partially defining said access opening and disposed in accessible relation with said tip cap.

11. The tamper evident closure as recited in claim 10 wherein said aperture includes a larger transverse dimension than a connector segment of the medical device and a smaller transverse dimension than at least a portion of said tip cap.

12. The tamper evident closure as recited in claim 10 wherein said indicator member further comprises an outer segment fixedly secured to said outer peripheral ridge of said open end of said housing; said outer segment directly attached in contiguous relation to said inner segment.

13. The tamper evident closure as recited in claim 12 wherein said cover is removably disposed in overlying engagement with at least a majority of said outer surface of said indicator member and in overlying, covering relation to said aperture.

14. The tamper evident closure as recited in claim 10 wherein at least said inner segment is formed of a tearable, paper-based material.

15. The tamper evident closure as recited in claim 10 wherein at least said inner segment is formed of a tearable, tape-based material.

16. The tamper evident closure as recited in claim 1 wherein said cover is at least partially formed of a gas permeable material.

17. A tamper evident closure for a medical device, said tamper evident closure comprising:
   a housing including an open end and a tip cap disposed within said housing,
   an indicator member connected to said housing in overlying, at least partially covering relation to said open end,
   said indicator member including an access opening disposed in accessible relation with an interior of said housing and said tip cap,
   said indicator member including an inner segment and an outer segment; said outer segment fixedly connected to an outer peripheral ridge of said open end,
   said inner segment directly connected in contiguous relation to said outer segment and extending inwardly therefrom in overlying and at least partially covering relation to said open end of said housing,
   a cover removably connected to an outer surface of at least said inner segment in overlying, covering relation to said access opening, and
   said inner segment formed of a rupturable material structured to rupture upon passage of said tip cap through said indicator member via said access opening subsequent to removal of said cover.

18. The tamper evident closure as recited in claim 17 wherein said access opening includes a larger transverse dimension than a connector segment of the medical device and a smaller transverse dimension than at least a portion of said tip cap.

19. The tamper evident closure as recited in claim 17 further comprising a removable adhesive connection disposed in interconnecting relation between an under portion of said cover and said outer surface of said inner segment.

20. The tamper evident closure as recited in claim 17 wherein said cover is at least partially formed of a gas permeable material.

21. The tamper evident closure as recited in claim 17 wherein at least said inner segment is formed of a tearable, paper-based material.

22. The tamper evident closure as recited in claim 17 wherein at least said inner segment is formed of a tearable, tape-based material.

\* \* \* \* \*